United States Patent [19]
Hohn et al.

[11] Patent Number: 5,190,699
[45] Date of Patent: Mar. 2, 1993

[54] CITRIC ACID FATTY ALCOHOL ESTER POLYGLYCOL ETHER SULFOSUCCINATES, PROCESS FOR THEIR PREPARATION AND THEIR USE

[75] Inventors: Elke Hohn; Hans-Jürgen Kohle, both of Schlüchtern; Georg-Friedrich Urban, Bensheim; Joachim Weigand, Freigericht; Christl Möller, Steinau a.d. Str., all of Fed. Rep. of Germany

[73] Assignee: REWO Chemische Werke GmbH, Steinau an der Strasse, Fed. Rep. of Germany

[21] Appl. No.: 863,832

[22] Filed: Apr. 6, 1992

[30] Foreign Application Priority Data

Apr. 11, 1991 [DE] Fed. Rep. of Germany ....... 4111811

[51] Int. Cl.$^5$ .............. A61K 7/075; A61K 7/50; C11D 1/06; C11D 1/26
[52] U.S. Cl. ................... 252/557; 252/121; 252/538; 252/173; 252/DIG. 5; 252/DIG. 13; 424/70; 554/88; 554/96; 554/97; 560/150; 560/151
[58] Field of Search .......... 560/150, 151; 554/88, 554/96, 97; 252/121, 538, 557, 173, DIG. 5, DIG. 13; 424/70

[56] References Cited

U.S. PATENT DOCUMENTS

| | | | |
|---|---|---|---|
| 2,076,111 | 4/1937 | Bannister | 260/103 |
| 3,404,164 | 10/1968 | Dutton | 560/150 |
| 3,948,976 | 4/1976 | Suen et al. | 260/484 P |
| 3,968,047 | 7/1976 | Smeets | 252/95 |
| 4,117,237 | 9/1978 | Longley | 560/151 |
| 4,250,050 | 2/1981 | Asbeck et al. | 252/354 |
| 4,299,975 | 11/1981 | Asbeck et al. | 560/151 |
| 4,426,310 | 1/1984 | Verunica | 252/106 |
| 4,749,515 | 6/1988 | Miyamoto | 252/545 |
| 4,866,203 | 9/1989 | Weil | 560/180 |
| 4,992,263 | 2/1991 | Tesmann et al. | 424/63 |
| 5,015,414 | 5/1991 | Kamegai | 252/545 |

FOREIGN PATENT DOCUMENTS 0199131 10/1986 European Pat. Off.
0334482 9/1989 European Pat. Off.

OTHER PUBLICATIONS

J. D. Malkemus, "Production of Alkylene Oxide Derivatives," *J. of Am. Oil Chem. Soc.*, 33: 571-574 (1956).
S. R. Epton, "A Rapid Method of Analysis for Certain Surface-Active Agents," *Nature*, 160: 795-796 (1947).

*Primary Examiner*—Dennis Albrecht
*Attorney, Agent, or Firm*—Scully, Scott, Murphy & Presser

[57] ABSTRACT

Disclosed are citric acid fatty alcohol ester polyglycol ether sulfosuccinates of the general formula (1)

$$\begin{array}{l} H_2C-COO-(CHR-CH_2-O)_a-R^1 \\ | \\ HO-C-COO(CHR-CH_2-O)_b-R^2 \\ | \\ H_2C-COO(CHR-CH_2-O)_c-R^3 \end{array} \quad (1)$$

and personal care products containing them, in which each R is the same or different and is H or -CH$_3$;

$$R^1 \text{ is } -CO-CH-CH_2-COO-X^+ \text{ or} \\ \phantom{R^1 \text{ is } -CO-}| \\ \phantom{R^1 \text{ is } -CO-CH-}SO_3-X^+$$

$$-CO-CH_2-CH-COO-X^+ \\ \phantom{-CO-CH_2-CH-}| \\ \phantom{-CO-CH_2-CH-}SO_3-X^+$$

R$^2$ is selected from the group consisting of $$-CO-CH-CH_2-COO-X^+, \quad -CO-CH_2-CH-COO-X^+, \\ \phantom{-CO-}| \phantom{-CH_2-COO-X^+, \quad -CO-CH_2-}| \\ \phantom{-CO-}SO_3-X^+ \phantom{-CH_2-COO-X^+, \quad -CO-CH_2-}SO_3-X^+$$

—H, and alkyl and acyl radicals having 8-22 carbon atoms, which radicals are optionally substituted and optionally contain one or more multiple bonds;
R$^3$ is an alkyl or acyl radical having 8-22 carbon atoms, which is optionally substituted and optionally contains multiple bonds;
a and b, which are identical or different, are each 0-5, provided that the sum of (a+b) is at least 1;
c is 0-15; and
X$^+$ is in each occurrence H$^+$ or a cation.

14 Claims, No Drawings

CITRIC ACID FATTY ALCOHOL ESTER POLYGLYCOL ETHER SULFOSUCCINATES, PROCESS FOR THEIR PREPARATION AND THEIR USE

The invention relates to novel citric acid fatty alcohol ester polyglycol ether sulfosuccinates, a process for their preparation and their use as cleaning agents and for cosmetic preparations.

Cosmetic preparations, in particular those which come within the area of hair and body cleaning, such as shower baths, foam baths, hair shampoos and liquid soaps, contain as cleaning components mainly anionic surfactants such as carboxylates, alkyl sulfates and alkyl ether sulfates, and sulfosuccinates.

These preparations should clean the skin surface, preferably only the film adhering to it, which can consist of body secretions such as perspiration and fats, flakes of skin or deposited dirt from the environment. The cleaning agents should in no case dry out the skin, irritate it or impair its natural function.

As the preparations can lead, however, during their frequent—in recent years almost daily—use to irritations of the skin, in order to improve the skin and eye mucosa compatibility frequent use is additionally made of so-called mild surfactants, such as, for example, betaines, protein derivatives, ampholytes, alkyl ether carboxylates and sulfosuccinates.

Especially for baby care agents and baby shampoos, particular value is placed on extremely low contents of substances irritating the skin and eye mucosa. The anionic surfactants conventionally used because of their excellent cleaning and foam-forming properties can be rendered substantially milder in their irritant action by means of the known mild cosurfactants, but in practice improvements, in particular with respect to eye mucosa compatibility, are still required.

In high concentrations or on their own, the mild surfactants are substantially irritation-free, but then have no practice-related foaming and cleaning properties and have unsatisfactory viscosities.

A further criterion for the usefulness of the surface-active substances is their toxicity. The toxicity lies in the surfactants themselves or products thereof formed by interaction with the constituents of the recipe.

Thus, the fatty acid alkanolamides hitherto readily additionally used because of their advantageous application and skin-caring properties have recently been employed only reluctantly in cosmetic preparations, as the residual content of free diethanolamine remaining in the preparation cannot be excluded and can thus give rise to nitrosamine formation (EP-A-0,306,843). N-Nitrosamines are carcinogenic in animal experiments.

As a result of increased environmental awareness, products are additionally required which are based on natural, renewable raw materials, have no toxicity whatsoever and can be degraded in the communal sewage plants rapidly and completely without toxic intermediates.

The products introduced in practice based on citric acid such as, for example, the mono-and/or difatty acid ester alkoxylates based on glycerol do have low toxicities and are mild products which do not irritate the skin, but with respect to their cleaning action or solubility they may not meet the requirements in practice.

The object of the present invention is to overcome these disadvantages of the prior art and to make available mild, skin-compatible cleaning agents for the household and industry, and cosmetic preparations, in particular those which fall within the area of hair and body cleaning.

This object has been achieved by the sulfosuccinates according to the invention based on citric acid which contain additionally alkoxylated ester groups. The invention relates in one aspect to citric acid fatty alcohol ester polyglycol ether sulfosuccinates of the general formula

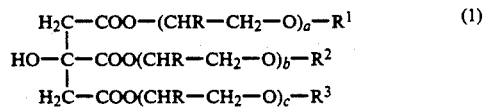

in which each
R is the same or different and is H or —CH$_3$;

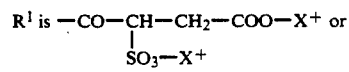

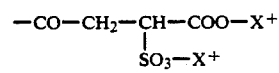

R$^2$ is selected from the group consisting of

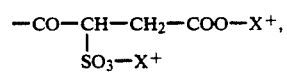

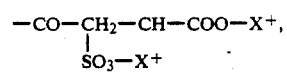

—H, and alkyl and acyl radicals having 8–22 carbon atoms, preferably 12–18 carbon atoms, which radicals are optionally substituted and optionally contain one or more multiple bonds;

R$^3$ is an alkyl or acyl radical having 8–22 carbon atoms, preferably 12–18 carbon atoms, which is optionally substituted and optionally contains multiple bonds;

a and b, which are identical or different, are each 0–5, preferably 1–3, provided that the sum of (a+b) is at least 1 and preferably at least 2, and more preferably the sum is 2–5;

c is 0–15, preferably 1–10; and

X$^+$ is in each occurrence H$^+$ or a cation.

The invention further relates to a process for the preparation of compounds of the general formula (1).

The invention further relates to aqueous hair-cleaning and care agents, washing-up liquids, all-purpose cleaners, neutral cleaners, and skin-care and cleaning agents, which are characterized in that they contain 1–10, preferably 2–8, parts by weight of at least one of the compounds of the general formula (1), defined amounts of at least one surfactant from the group comprising the nonionic, amphoteric, zwitterionic and ionic surfactants, preferably 0.1 to 30 parts by weight, if desired 0.1 to 15 parts by weight of one of the customary agents from the group comprising additives and auxiliaries, thickeners, fragrances, colorants and vegetable extracts, and if desired water to 100.

Further embodiments of the invention are characterized by the claims.

One starting substance for the preparation of the compounds of the general formula (1) according to the invention is natural or synthetic citric acid. Depending on the requirements for the final product, a highly purified grade or the commercial material of technical purity can be employed here.

The citric acid can be reacted in a first step with one or two mol of fatty alcohol or alkoxylated fatty alcohol according to the known methods to give the ester (U.S. Pat. No. 2,076,111, U.S. Pat. No. 3,948,976, EP 0,199,131). According to the invention, the monoesters are preferred.

The alcohols used are the monofunctional fatty alcohols having 8-22 carbon atoms, preferably the naturally occurring fatty alcohols, and also the fatty alcohols which can be prepared by known processes from synthetic or natural fatty acids, such as lauryl alcohol, palmityl alcohol, stearyl alcohol, oleyl alcohol, linolyl alcohol, tallow alcohol and the alcohols based on natural coconut fatty acids.

Synthetic alcohols, such as, for example, the compounds prepared by oxo synthesis or by the Guerbet reaction, are also utilizable.

The alcohols can be employed as such or in the form of the alkoxylated, preferably ethoxylated and/or propoxylated, alcohols containing at least one ether group obtained from these alcohols by known processes.

According to the invention, alkoxylation products where c is 1-15, preferably 1-10 and 11 alkoxy units/mole of fatty alcohol are preferred (U.S. Pat. No. 4,866,203 and the references cited therein).

Instead of reacting citric acid with fatty alcohol alkoxylates and then with fatty acids, fatty acids which have already been alkoxylated, preferably ethoxylated and/or propoxylated, by known processes can then be reacted with the citric acid (EP-A-0,334,482). The degrees of alkoxylation of the fatty acids correspond with those of the fatty alcohol alkoxylates as described herein. In these products $R^3$ of the general formula (1) is preferably an acyl radical.

The fatty acids used are the monobasic acids having 8-22 carbon atoms, preferably the naturally occurring acids, such as lauric acid, palmitic acid, stearic acid, oleic acid, linoleic acid, linolenic acid, ricinoleic acid, coconut fatty acid or mixtures thereof.

The esters can be prepared in a second step by processes known per se (J. Am. Oil Chemist's Soc., 1956, 33, 571, EP-A-0,334,482) with alkylene oxides such as, in particular, ethylene oxide and propylene oxide to give the polyglycol ether esters, where, in the statistical mean, 0-5, preferably 1-3, mol of alkylene oxide are adducted per carboxyl group. It has been found that the products according to the invention having a total (a+b) of the general formula (1) of at least 1, preferably of at least 2, mol of alkylene oxide give excellent results. In particularly preferred products according to the invention (a+b) is between 2 and 5.

The citric acid can also be alkoxylated in a first step by the abovementioned known processes and reacted in a second step with 1 or 2 mol of fatty acid to give the fatty acid ester, where $R^3$ is also an acyl radical and the sum of (a+b+c) is 1-25, preferably 5-15 and in particular 3-5.

The reaction to give the sulfosuccinate is carried out with maleic anhydride and subsequent sulfonation with sodium sulfite by processes known per se (German published specification 2,700,072).

Reaction in this case is carried out by stirring the intermediate prepared as described above with one mol of maleic anhydride per mole of hydroxyl group to be reacted at 60-80° C. until the anhydride has reacted completely. The maleic acid hemiester is then added to an aqueous sodium sulfite solution (1 equivalent of sulfite per equivalent of hemiester) and sulfonated at 60-80° C. until the sulfite has completely reacted. The aqueous product is then adjusted to neutral pH.

In general, according to the invention, the process is carried out by esterifying, in a first step, the citric acid monoester with the fatty alcohol or the fatty alcohol alkoxylate, if appropriate additionally using an esterification catalyst, at 140°-160° C. with removal of the water of reaction, reacting this ester in a second step in the presence of a basic catalyst at 80°-150° C. and 1-10 bar with alkylene oxide to give the alkoxylate which is reacted in a third step by addition of maleic anhydride at 60°-80° C. to give the hemiester and in a last step at 60°-80° C. with aqueous sodium sulfite solution to give the salt of the corresponding sulfonic acid.

The compounds according to the invention are shown in idealized form by the general formula (1). In addition to the monofatty acid esters or difatty acid esters indicated, the technical mixtures still contain small amounts of the higher esters, and the degrees of alkoxylation indicated are as statistical means.

Purification is not necessary for use according to the invention, that is to say technical mixtures can be reused directly as such.

The mixtures according to the invention for cleaning purposes and cosmetics in general exist as aqueous compositions or as aqueous alcoholic solutions, creams, emulsion or gels and, for adaptation to the intended application, can contain the auxiliaries and additives customary in each case and which are additionally used for the preparation of cleaning agents and cosmetic preparations in the area of hair and body cleaning, that is to say are customary for shower baths, foam baths, shampoos, liquid soaps, baby care agents and detergents as well as for mild cleaning agents such as washing-up liquids, all-purpose cleaners or neutral cleaners for manual use.

For cosmetic applications, the surfactants, fragrances, preservatives, colorants, vegetable extracts and other cosmetic additives customary in these fields may additionally be used.

In addition to the known betaines, amphoteric and nonionic compounds, suitable surfactants for the cleaning formulation are in particular the anionic surfactants such as carboxylates, alkyl sulfates, alkyl ether sulfates, alkyl sulfonates, alkyl ether sulfonates, and alkyl sulfosuccinates. Those preferred according to the invention are alkylamidobetaines such as REWOTERIC® [1] AM B 13 and AM B 14, carboxyglycinates such as REWOTERIC® AM 2 C NM, carboxypropionates such as REWOTERIC® AM KSF 40, sulfobetaines such as REWOTERIC® AM CAS, anionic surfactants such as ether sulfates REWOPOL® [2] NL 3, ether carboxylates such as REWOPOL® CLN 100, sulfosuccinates such as REWOPOL® SB FA 30, REWOPOL® SBZ, REWODERM® [3] SPS, nonionic surfactants such as glycerol fatty acid ester ethoxylates such as REWODERM® ES 90, glycerol monostearate such as REWOMUL® [2] MG, and cetyl alcohol (wherein [1], [2], [3] and [4] are trademarks of REWO Chemische Werke GmbH, Steinau an der Strabe, Germany).

The compounds according to the present invention can be employed in shampoos, advantageously in amounts from 1-10 parts by weight, in particular 2-8 parts by weight; in creams, advantageously in amounts from 1-7 parts by weight, preferably 1-5 parts by weight; and in cleaning agents, advantageously in amounts from 1-5, preferably 1.5-3 parts by weight. In addition to the compound or compounds of formula (1), the other surfactants in the shampoos are customarily additionally used in amounts of 1-20 parts by weight, preferably 5-15 parts by weight, and in the creams in amounts from 1-10 parts by weight, preferably 2-5 parts by weight.

The thickeners employed are 1-8 parts by weight of one or more compounds effective to thicken the desired formulation. Customary in this field include glycerol fatty acid ester ethoxylates, fatty alcohol ethoxylates, fatty acid alkanolamides and the alkali metal, alkaline earth metal and ammonium salts customary as thickeners, which are soluble in water at 20° C. in amounts of at least 1% by weight, such as, in particular NaCl and NH$_4$Cl.

The analytical values mentioned in the following examples are determined by the following methods which are generally customary in this field:

Acid Value (AV)

The acid value is a measure of the free acid content of a fat or of technical fatty acids and gives the number of milligrams of potassium hydroxide which are necessary to neutralize 1 gram of substance.

The values are determined according to the DGF standard method C-V4.

CONTENT OF DRY MATTER

The content is determined by heating and drying to constant weight at 105° C.

Hydroxyl Value (OHV)

The hydroxyl value is used to determine the content of hydroxyl groups and gives the number of milligrams of potassium hydroxide which are necessary to neutralize the acetic acid consumed by 1 gram of fat during the acetylation (mg KOH/g).

Benzavlon-WAS

The content of wash-active substance (B-WAS) given in the following examples is titrated by the customary two-phase titration using benzalkonium chloride against Methylene Blue as indicator (cf. S.R. Apton, Nature (London) 160, 1967, P. 795).

PREPARATION OF THE COMPOUNDS ACCORDING TO THE INVENTION

EXAMPLE 1

1.1 Esterification 377 g (1.79 mol) of citric acid monohydrate, 723.6 g (1.97 mol) of REWOPAL ® LA 4* and 1.3 g of hypophosphorous acid were poured under nitrogen into a reaction vessel equipped with a stirrer, thermometer, water separator and condenser.

The reaction product has an acid value of 200.

*=Product and trademark of REWO Chemische Werke GmbH; C$_{12/14}$ fatty alcohol ethoxylate with 4 ethylene oxide units (EO) and an OHV of 153.

The mixture was heated to 140° C. under an N$_2$ atmosphere and with good stirring and was kept at this temperature for 2 h. During this period, almost the theoretical amount of water of reaction distilled off. After the reaction mixture had been cooled to 80° C., the pressure was slowly reduced to 20 mbar and the reaction was completed at this pressure and 140° C.

1.2 Ethoxylation 784 g of citric acid monoester from Example 1.1 were reacted with 119 g of ethylene oxide in portions in an autoclave at 90° C. after addition of 4 g of alkyldimethylamine, so that the pressure was at most 5 bar.

| Analytical data: | |
|---|---|
| Acid value | 24.6 mg of KOH/g |
| Hydroxyl value | 187.3 mg of KOH/g |

1.3 Hemiester formation 333 g (1.2 mol) of ethoxylate from Example 1.2 were treated with 98 g (1.0 mol) of maleic anhydride at 70-80° C. under N$_2$ and the mixture was stirred at this temperature for 2 h. The reaction product had the following analytical values:

| Acid value in acetone | 148.2 mg of KOH/g |
|---|---|
| Acid value in isopropanol | 140.2 mg of KOH/g |

1.4 Sulfonation 350 g of hemiester from Example 1.3 were slowly added dropwise at 60-70° C. to a solution of 108 g (1.0 mol) of sodium sulfite in 680 g of water. The solution had the following analytical data:

| Dry residue | 40.4% |
|---|---|
| Benzavlon WAS | 34.3% |
| pH (5%) | 6.1 |

Example 2

2.1 Esterification 210 g (1 mol) of citric acid monohydrate, 507 g (1.1 mol) of REWOPAL ® LA 6* and 1.3 g of hypophosphorous acid were poured under N$_2$ into a reaction vessel equipped with a stirrer, thermometer, water separator and condenser.

*=Product and trademark of REWO Chemische Werke GmbH; C$_{12/14}$ fatty alcohol ethoxylate with 6 ethylene oxide units (EO) and an OHV of 130.

The mixture was heated to 140° C. under a nitrogen atmosphere and with good stirring and was kept at this temperature for 2 h. During this time, almost the theoretical amount of water of reaction distilled off. The reaction mixture was allowed to cool to 80° C. and a vacuum of 20 mbar was applied to complete the reaction. The acid value of the final product was 173.

2.2 Ethoxylation 610 g of citric acid monoester from Example 2.1 were reacted with 116 g of ethylene oxide in portions in an autoclave at 90° C. after addition of 3 g of alkyldimethylamine so that the pressure was at most 5 bar.

| Analytical data: | |
|---|---|
| Acid value | 6.7 mg of KOH/g |
| Hydroxyl number | 185 mg of KOH/g |

2.3 Hemiester formation 363 g (1.2 mol) of ethoxylate from Example 2.2 were treated with 98 g (1 mol) of maleic anhydride at 70–80° C. under $N_2$ and the mixture was stirred at this temperature for 2 h. The reaction product had the following analytical values:

| Acid value in acetone | 150 mg of KOH/g |
|---|---|
| Acid value in isopropanol | 137 mg of KOH/g |

2.4 Sulfonation 350 g of hemiester from Example 2.3 were slowly added dropwise at 60–70° C. to a solution of 101 g (1 mol) of sodium sulfite in 680 g of water. The solution had the following analytical data:

| Dry residue | 39.7% |
|---|---|
| Benzavlon WAS | 28.4% |
| pH (5%) | 6.3 |

Example 3

3.1 Esterification 141 g (0.67 mol) of citric acid monohydrate, 470 g (0.73 mol) of REWOPAL ® LA 10* and 1 g of hypophosphorous acid were poured under $N_2$ into a reaction vessel equipped with a stirrer, thermometer, water separator and condenser.

*=Product and trademark of REWO Chemische Werke GmbH; $C_{12/14}$ fatty alcohol ethoxylate with 10 ethylene oxide units (EO) and an OHV of 90.

The mixture was heated to 140° C. under a nitrogen atmosphere and with good stirring and was kept at this temperature for 2 h. During this time, almost the theoretical amount of water of reaction distilled off (acid value of the product: 121). The reaction mixture was allowed to cool to 80° C. and a vacuum of 20 mbar was applied to complete the reaction. The acid value of the final product was 113.

3.2 Ethoxylation 513 g of citric acid monoester from Example 3.1 were reacted with 60 g of ethylene oxide in portions in an autoclave at 90° C. after addition of 2.6 g of alkyl-dimethylamine so that the pressure was at most 5 bar.

| Analytical data: | |
|---|---|
| Acid value | 2.7 mg of KOH/g |
| Hydroxyl value | 108 mg of KOH/g |

3.3 Hemiester formation 478 g (0.9 mol) of ethoxylate from Example 3.2 were treated with 75 g (0.8 mol) of maleic anhydride at 70–80° C. under $N_2$ and the mixture was stirred at this temperature for 2 h. The reaction product had the following values:

| Acid value in acetone | 89.3 mg of KOH/g |
|---|---|
| Acid value in isopropanol | 82.8 mg of KOH/g |

3.4 Sulfonation 480 g of hemiester from Example 3.3 were slowly added dropwise at 60°–70° C. to a solution of 89 g (0.8 mol) of sodium sulfite in 850 g of water. The solution had the following analytical data:

| Dry residue | 39.2% |
|---|---|
| Benzavlon WAS | 28.9% |
| pH (5%) | 6.1 |

Example 4

4.1 Esterification 225 g (1.1 mol) of citric acid monohydrate, 506 g (1.1 mol) of REWOPAL ® TA 6* and 0.7 g of hypophosphorous acid were poured under $N_2$ into a reaction vessel fitted with a stirrer, thermometer, water separator and condenser.

*=Product and trademark of REWO Chemische Werke GmbH; $C_{16/18}$ fatty alcohol ethoxylate with 6 ethylene oxide units (EO) and an OHV of 120.

The mixture was heated to 140° C. under a nitrogen atmosphere and with good stirring and was kept at this temperature for 4 h. During this time, almost the theoretical amount of water of reaction distilled off. The reaction solution was allowed to cool to 90° C. and a vacuum of 20 mbar was applied to complete the reaction. The acid value of the final product was 173.

4.2 Ethoxylation 635 g of citric acid monoester from Example 4.1 were reacted with 97 g of ethylene oxide in portions in an autoclave at 90° C. after addition of 3 g of alkyldimethylamine so that the pressure was at most 5 bar.

| Analytical data: | |
|---|---|
| Acid value | 26 mg of KOH/g |
| Hydroxyl number | 138 mg of KOH/g |

4.3 Hemiester Formation 293 g (0.7 mol) of ethoxylate from Example 4.2 were treated with 59 g (0.6 mol) of maleic anhydride at 70°–80° C. under $N_2$ and the mixture was stirred at this temperature for 2 h. The reaction product had the following analytical values:

| Acid number in acetone | 133 mg of KOH/g |
|---|---|
| Acid number in isopropanol | 122 mg of KOH/g |

4.4 Sulfonation 293 g of hemiester from Example 4.3 were slowly added dropwise at 60°-70° C. to a solution of 66 g (0.6 mol) of sodium sulfite in 535 g of water. The solution had the following analytical data:

| Dry residue | 39.4% |
|---|---|
| Benzavlon WAS | 28.9% |
| pH (5%) | 6.4 |

Example 5

5.1 Esterification 210 g (1 mol) of citric acid monohydrate, 735 g (2 mol) of REWOPAL.® LA 4* and 1 g of hypophosphorous acid were poured under $N_2$ into a reaction vessel equipped with a stirrer, thermometer, water separator and condenser.

*=Product and trademark of REWO Chemische Werke GmbH; $C_{12/14}$ fatty alcohol ethoxylate with 4 ethylene oxide units (EO) and an OHV of 153.

The mixture was heated to 140° C. under a nitrogen atmosphere and with good stirring and was kept at this temperature for 2 h. During this time, almost the theoretical amount of water of reaction distilled off. The reaction mixture was allowed to cool to 80° C. and a vacuum of 20 mbar was applied to complete the reaction. The acid value of the final product was 68.

5.2 Ethoxylation 837 g of citric acid monoester from Example 5.1 were reacted with 45 g of ethylene oxide in portions in an autoclave at 90° C. after addition of 4.1 g of alkyldimethylamine so that the pressure was at most 5 bar.

| Analytical data: | |
|---|---|
| Acid value | 10.6 mg of KOH/g |
| Hydroxyl value | 92.4 mg of KOH/g |

5.3 Hemiester formation 364 g (0.6 mol) of ethoxylate from Example 5.2 were treated with 59 g (0.6 mol) of maleic anhydride at 70°-80° C. under $N_2$ and the mixture was stirred at this temperature for 2 h. The reaction product had the following analytical values:

| Acid value in acetone | 103 mg of KOH/g |
|---|---|
| Acid value in isopropanol | 92 mg of KOH/g |

5.4 Sulfonation 352 g of hemiester from Example 5.3 were slowly added dropwise at 60°-70° C. to a solution of 66 g (0.6 mol) of sodium sulfite in 625 g of water. The solution had the following analytical data:

| Dry residue | 39.4% |
|---|---|
| Benzavlon WAS | 27.8% |
| pH (5%) | 6.9 |

Cosmetic Formulations

The formulations below can be prepared by simply stirring the constituents into water.

All formulations are given in percent by weight calculated relative to solids content.

The following table lists the CTFA-accepted names of the ingredients used in the following Examples. They are identified in the table with the reference numerals that appear in the following Examples as superscripts:

1 = Disodium PEG-4 cocoamido MIPA-sulfosuccinate
2 = Disodium lauroamphodiacetate (and) sodium lauryl sulfate (and) hexylene glycol
3 = Cocoamidopropyl hydroxysultaine
4 = Ricinoleamidopropyltrimonium methosulfate
5 = PEG-200 glyceryl tallowate mod.
6 = Disodium laureth sulfosuccinate
7 = Sodium laureth sulfate
8 = Cocoamidopropyl betaine
9 = PEG-200 glyceryl tallowate
10 = Disodium cocoamphodiacetate
11 = PEG-80 glyceryl tallowate
12 = Cocoamidopropyl betaine
13 = Glyceryl stearate
14 = Laureth-6

ANALYTICAL METHODS

Calcium hardness compatibility: DIN 53 905
Skin compatibility (Zein Test):
Götte, Ernst, Chem. Phys. Appl. Surface Active Subst. Proc. Int. Congr.4 (1964) 83–90:
  <200 mg of N/100 ml = non-irritating
  200–400 mg of N/100 ml = slightly irritating
  >400 mg of N/100 ml = irritating
Surface tension: Dr. R. Hensch; Fetter, Seifen, Anstrichmittel, 72 (1970), P. 969–977
Viscosity: Brookfield rotary viscometer (cup and spindle) measured at 20° C. according to the instructions of the apparatus manufacturer.

Determination of the foaming power according to Ross Miles following DIN 53902 part 2 with the modification that the following DIN 53902 part 2 with the modification that the following measurements and amounts were used:

| Internal diameter of the outlet nozzle: | 3.5 mm |
|---|---|
| Fall height of the sample solution: | 940 mm |
| Amount of sample solution introduced: | 50 ml |
| Amount of sample solution run in: | 200 ml |
| Measurement temperature | 40° C. |
| Solvent | demineralized water |

| Basic formulation: Skin-cleaning agent and make-up remover for sensitive skin | |
|---|---|
| Compound according to the invention | 2-8 parts by weight |
| REWOTERIC ®* AM B 14[12] | 2-8 parts by weight |
| Hydroxyethylcellulose | 0.2-1.5 parts by weight |
| demin. water | to 100 |

| Basic formulation: Skin cream | |
|---|---|
| Compound according to the invention | 1-5 parts by weight |
| Glycerol monodistearate | 2-10 parts by weight |
| Cetyl alcohol | 1-4 parts by weight |
| Liquid paraffin 3.5° E | 4-12 parts by weight |
| Glycerol | 1-5 parts by weight |
| demin. water | to 100 |
| Preservative | as required |

Basic formulation: Washing-up liquid

| Compound according to the invention | | |
|---|---|---|
| REWOPOL ®* NL 3-28[7] | 1-10 | parts by weight |
| REWOTERIC ® AM CAS[3] | 1-30 | parts by weight |
| REWOPOL ® LA 6[14] | 1-5 | parts by weight |
| demin. water | 1-10 | parts by weight |
|  | to 100 | |
| Basic formulation: Shower bath | | |
| Compound according to the invention | 2-8 | parts by weight |
| REWOTERIC ® AM g 30[2] | 5-15 | parts by weight |
| REWOTERIC ® AM CAS[3] | 2-6 | parts by weight |
| REWOQUAT ®* RTM 50[4] | 1-3 | parts by weight |
| REWODERM ®* Li P 75[5] | 1-4 | parts by weight |
| demin. water | to 100 | |
| Basic formulation: Hair shampoo | | |
| Compound according to the invention | 2-8 | parts by weight |
| REWOPOL ® NL 3-28[7] | 4-10 | parts by weight |
| REWOTERIC ® AM B 13[8] | 2-8 | parts by weight |
| REWODERM ® Li 420-70[9] | 1-4 | parts by weight |
| demin. water | to 100 | |
| Basic formulation: Baby shampoo | | |
| Compound according to the invention | 2-8 | parts by weight |
| REWOTERIC ® AM 2 C NM[10] | 2-8 | parts by weight |
| REWOTERIC ® AM B 13[8] | 4-12 | parts by weight |
| REWOPOL ® NL 3-28[7] | 2-10 | parts by weight |
| REWODERM ® Li 48-50[11] | 1-4 | parts by weight |
| demin. water | to 100 | |

* = Trademark of REWO Chemie Werke GmbH, Steinau an der Straße, Germany

TABLE 1

| Compound according to example | a + b | c | x | y z m | n |
|---|---|---|---|---|---|
| 1.4 | 2 | 4 | 1.0 | y 0.4 z 0.6 m — | 12/14 |
| 2.4 | 2.7 | 6 | 1.0 | y 0.4 z 0.6 m — | 12/14 |
| 3.4 | 2.7 | 10 | 1.0 | y 0.4 z 0.6 m — | 12/14 |
| 4.4 | 2.7 | 6 | 1.0 | y 0.4 z 0.6 m — | 18 |
| 5.4 | 5 | 4 | 1.0 | y 0 z 0 m 1 | 12/14 | x is the number of sulfosuccinate groups $R^1$ per molecule
y is the number of $R^2$ groups per molecule which are —H
z is the number of $R^2$ groups per molecule which are sulfosuccinate
m is the number of $R^2$ groups per molecule which are alkyl or acyl (as defined for $R^3$)
n is the number of carbon atoms in the $R^3$ alkyl or acyl chain

TABLE 2

| Example from Table 1 | Foaming power [mm] immediately | Foaming power [mm] after 5 min | Calcium hardness compatability points | Calcium hardness compatability grading | Zein test mg of N/100 ml | Surface tension Lecomte du Nouy (ring method) mN/m 0.1% | Surface tension Lecomte du Nouy (ring method) mN/m 0.01% |
|---|---|---|---|---|---|---|---|
| Example 1.4 | 150 | 140 | 75 | V | 25 | 33.7 | 35.7 |
| Example 2.4 | 155 | 150 | 75 | V | 30 | 33.3 | 35.2 |
| Example 3.4 | 145 | 140 | 75 | V | 12 | 37.7 | 37.9 |
| Example 4.4 | 100 | 70 | 75 | V | 41 | 43.5 | 44.8 |
| Example 5.4 | 140 | 130 | 75 | V |  | 32.0 | 34.9 |
| Comparison example REWOPOL ® NL 3-28 | 200 | 180 | 75 | V | 300 | 34.2 | 32.9 |
| Comparison example REWOPOL ® SB FA 30 | 170 | 160 | 75 | V | 250 | 28.0 | 31.4 |

Test Formulation: Shower Bath

The examples according to the invention have been assessed in the test formulation by a test panel of 20 persons (female and male) with respect to
foaming power
feeling of the skin
feeling of the dried skin
Skin compatibility: Reduction of the zein values in recipe of Table 4.

TABLE 3

| Formulation | 1 | 2 | 3 |
|---|---|---|---|
| Example 1.4 | — | 4 | — |
| Example 3.4 | — | — | 4 |
| REWOPOL ® SB Z[1] | 4 | — | — |
| REWOTERIC ® AM G 30[2] | 10.5 | 10.5 | 10.5 |
| REWOTERIC ® AM CAS[3] | 3 | 3 | 3 |
| REWOQUAT ® RTM 50[4] | 1 | 1 | 1 |
| REWODERM ® Li S 75[5] | 2.3 | 2.3 | 2.3 |
| demin. water | to 100 | to 100 | to 100 |
| pH, adjusted with citric acid | 6.5 | 6.5 | 6.5 |
| Viscosity [mPas] | 3000 | 3000 | ~2500 |
| Foaming power [nm] | 195/185 | 205/195 | 200/195 |
| Foaming power[4] | good | good | good |
| Foam structure[4] | having creamy, minute bubbles | creamy, having minute bubbles | creamy, having minute bubbles |
| Feeling of the skin, wet skin[4] | relatively smooth | smooth | smooth |
| Feeling of the skin, dry skin[4] | relatively smooth | smooth | smooth |

[4] = The assessment was carried out according to a graded assessment system, the abovementioned assessment representing the arithmetic mean.

TABLE 4

| Test Formulation: Skin compatibility preparation, reduction of zein values | 1 | 2 | 3 | 4 |
|---|---|---|---|---|
| Example 3.4 | — | 4.5 | — | — |
| Example 1.4 | 4.5 | — | — | — |
| REWOPOL ® SB FA 30[6] | — | — | 4.5 | — |
| REWOPOL ® NL 3-28[7] | 10.5 | 10.5 | 10.5 | 15 |
| demin. water | 85 | 85 | 85 | 85 |
| pH, adjusted with citric acid | 6.5 | 6.5 | 6.5 | 6.5 |

TABLE 4-continued

| Test Formulation: Skin compatibility preparation, reduction of zein values | | | | |
|---|---|---|---|---|
| | 1 | 2 | 3 | 4 |
| Assessment of foam quality | creamy having minute bubbles | creamy having minute bubbles | having minute bubbles | large bubbles |
| Feeling after washing on the dry skin | pleasantly smooth | pleasantly smooth | soft | somewhat rough |
| Zein values skin compatibility | 180 mg of N/100 ml | 180 mg of N/100 ml | 270 mg of N/100 ml | 300 mg of N/100 ml |

Test formulation: Hair shampoo

The examples according to the invention have been assessed in the formulation by 10 test persons experienced in application for
combability
volume of the hair and hold of the hairstyle.

TABLE 5

| Formulation | 1 | 2 | 3 |
|---|---|---|---|
| Example 1.4 | — | 3 | — |
| Example 2.4 | — | — | 3 |
| REWOPOL ® NL 3-28[7] | 8 | 6 | 6 |
| REWOTERIC ® AM B 13[8] | 5 | 4 | 4 |
| REWODERM ® Li 420-70[9] | 2.1 | 2.1 | 2.1 |
| demin. water | to 100 | to 100 | to 100 |
| pH, adjusted with citric acid | 6.5 | 6.5 | 6.5 |
| Combability | 3 | 5-6 | 5-6 |
| Volume of the hair Set of the hairstyle | 3-4 | 6 | 6 |
| Viscosity [mPas] | ~3000 | ~12000 | ~12000 |
| Foam height [mm] | 195/185 | 195/185 | 195/185 |

Assessment of the combability:

1-3: difficult to comb through; the hair offers considerable resistance to the combing process
4-7: the hair can be combed through relatively easily; combing resistance is decreased; sufficient for a conditioning shampoo, depending on hair type
8-10: reserved for the subsequent after-treatment by so-called hair rinse agents

ASSESSMENT OF THE HAIR VOLUME AND THE SET OF THE HAIRSTYLE 1-3: the hair is dry or dull and lifeless; poor hold of the hairstyle
4-7: the hair is soft and bouffant, simultaneously with a good hold of the hairstyle
8-10: the hair is soft and smooth, but too loose; as a result the hairstyle does not have a good hold.

The assessment was carried out by a graded point system, the abovementioned assessment representing the arithmetic mean.

TABLE 6

| Test formulation: Baby shampoo or hair and body shampoo for sensitive skin | | | |
|---|---|---|---|
| Formulation | 1 | 2 | 3 |
| Example 1.4 | — | 3 | — |
| Example 2.4 | — | — | 3 |
| REWOTERIC ® AM 2C NM[10] | 3.5 | 3.5 | 3.5 |
| REWOTERIC ® AM B 13[8] | 7 | 7 | 7 |
| REWOPOL ® NL 3-28[7] | 7.5 | 4.5 | 4.5 |
| REWODERM ® Li 48-50[11] | 3 | 3 | 3 |
| demin. water | to 100 | to 100 | to 100 |
| pH, adjusted with citric acid | 6.5 | 6.5 | 6.5 |
| Foam height mm DIN 53 902 part 2 | 195/185 | 200/190 | 200/190 |
| Zein values, mg of N/100 ml (skin compatibility) | ~70 | ~70 | ~70 |
| Foam structure | having large bubbles | having fine bubbles | having fine bubbles |
| Feeling of the skin, wet and dry skin | somewhat rough | smooth soft | smooth soft |

TABLE 7

| Test formulation: Skin-cleaning agent and make-up remover for sensitive skin | | | |
|---|---|---|---|
| Formulation | 1 | 2 | 3 |
| Example 3.4 | — | — | 4 |
| Example 1.4 | — | 4 | — |
| REWOPOL ® SB FA 30[6] | 4 | — | — |
| REWOTERIC AM B 14[12] | 4.5 | 4.5 | 4.5 |
| Hydroxyethylcellulose | 0.5 | 0.5 | 0.5 |
| demin. water | to 100 | to 100 | to 100 |
| pH, adjusted with citric acid | 6.5 | 6.5 | 6.5 |
| Zein values mg of N/100 ml (skin compatibility) | about 170 | <50 | <50 |

The use of the sulfosuccinates according to the invention in the present recipe gives a very highly skin-compatible cleaning agent, which is seen in a lower zein value in comparison with the standard sulfosuccinate REWOPOL ® SB FA 30.

TABLE 8

| | Test Formulation Skin cream | | | |
|---|---|---|---|---|
| Formulation | 1 | 2 | 3 | 4 |
| Example 1.4 | — | — | 2 | — |
| Example 3.4 | — | — | — | 2 |
| Stearyl alcohol ethoxylate (3EO) | 2 | — | — | — |
| REWOMUL ® MG[13] | 6 | 6 | 6 | 6 |
| REWOPUL ® SB FA 30[6] | — | 2 | — | — |
| Cetyl alcohol | 2 | 2 | 2 | 2 |
| Liquid paraffin 3.5° E | 8 | 8 | 8 | 8 |
| Glycerol | 3 | 3 | 3 | 3 |
| Preservative | as required | as required | as required | as required |
| demin. water | to 100 | to 100 | to 100 | to 100 |
| Stability of the emulsion at 5° C., 20° C. and 40° C. | stable | unstable | stable | stable |

TABLE 8-continued

| Formulation | Test Formulation Skin cream | | | |
|---|---|---|---|---|
| | 1 | 2 | 3 | 4 |
| Appearance | smooth, white cream | greasy, emulsion breaks | smooth, white cream | smooth, white cream |

Assessment of the properties on the skin by 10 volunteers: more than 80% assessed the test recipes 3 and 4 as easy to spread on the skin
easily absorbed into the skin
the skin is smooth and soft, without becoming sticky and fatty.

The comparison recipe 1 is assessed as soft; recipe 2 is unstable.

TABLE 9

| | Test Formulation: Skin-compatible washing-up liquid for manual use | | | | | |
|---|---|---|---|---|---|---|
| Formulation | 1 | 2 | 3 | 4 | 5 | 6 |
| Example 3.4 | — | — | 3 | — | 1.5 | — |
| Example 1.4 | — | 3 | — | 1.5 | — | — |
| REWOPOL ® NL 3-28[7] | 18 | 18 | 18 | 18 | 18 | 18 |
| REWOTERIC ® AM CAS[3] | 1.5 | — | — | 1.5 | 1.5 | — |
| REWOPOL ® LA 6[4] | 1.5 | — | — | — | 1.5 | 3 |
| demin. water | to 100 | to 100 | to 100 | to 100 | to 100 | to 100 |
| Viscosity mPas adjusted with NaCl to about | 500 | 500 | 500 | 500 | 500 | 500 |
| Zein values (skin compatibility) | 220 | 220 | 180 | 180 | 200 | 250 |
| Foaming power [mm] | 195/185 | 195/185 | 190/185 | 190/185 | 190/185 | 190/180 |
| +0.5 ml of olive oil | 190/180 | 190/185 | 190/185 | 190/180 | 190/185 | 190/180 |
| +1.0 ml of olive oil | 190/185 | 190/185 | 190/185 | 185/180 | 190/185 | 190/180 |

What is claimed is:

1. A citric acid fatty alcohol ester polyglycol ether sulfosuccinate of the general formula (1)

$$\begin{array}{l} H_2C-COO-(CHR-CH_2-O)_a-R^1 \\ | \\ HO-C-COO(CHR-CH_2-O)_b-R^2 \\ | \\ H_2C-COO(CHR-CH_2-O)_c-R^3 \end{array} \qquad (1)$$

in which
each R is the same or different and is H or —$CH_3$;

$$R^1 \text{ is } \begin{array}{c} -CO-CH-CH_2-COO-X^+ \text{ or} \\ | \\ SO_3-X^+ \end{array}$$

$$\begin{array}{c} -CO-CH_2-CH-COO-X^+ \\ | \\ SO_3-X^+ \end{array}$$

$R^2$ is selected from the group consisting of

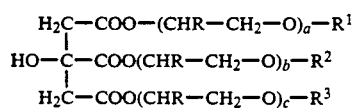

—H, and alkyl and acyl radicals having 8-22 carbon atoms, which radicals are optionally substituted and optionally contain one or more multiple bonds;
$R^3$ is an alkyl or acyl radical having 8-22 carbon atoms, which is optionally substituted and optionally contains multiple bonds;

a and b, which are identical or different, are each 0-5, provided that the sum of (a+b) is at least 1;
c is 0-15; and
$X^+$ is in each occurrence $H^+$ or a cation.

2. A compound of the general formula (1) as claimed in claim 1, wherein
R is H;
$R^1$ and $R^2$ are each selected from the group consisting of

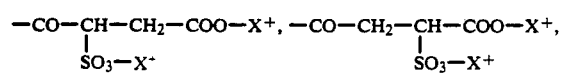

$R^3$ is an alkyl radical having 12-18 carbon atoms;
the sum of (a+b) is 2-5; and
c is 1-10.

3. A compound of the general formula (1) as claimed in claim 2, wherein the sum of (a+b+c) is 5-15, and $R^3$ is an acyl radical having 8-18 carbon atoms composed of the natural mixture of the coconut fatty acids.

4. A compound of the general formula (1) as claimed in claim 1, wherein $R^2$ is selected from the group consisting of alkyl and acyl radicals having 12-18 carbon atoms, which radicals are optionally substituted and optionally contain one or more double bonds.

5. A compound of the general formula (1) as claimed in claim 1, wherein $R^3$ is an alkyl or acyl radical having 12-18 carbon atoms, which is optionally substituted and optionally contains multiple bonds.

6. A compound of the general formula (1) as claimed in claim 1, wherein a and b are each preferably 1-3.

7. A compound of the general formula (1) as claimed in claim 1, wherein the sum of (a+b) is at least 2.

8. A compound of the general formula (1) as claimed in claim 1, wherein the sum of (a+b) is 2-5.

9. A compound of the general formula (1) as claimed in claim 1, wherein c is 1-10.

10. An aqueous hair-cleaning and care agent, comprising
a) 1-10 parts by weight of at least one compound of the general formula (1) of claim 1;

b) 1-20 parts by weight of at least one surfactant selected from the group consisting of nonionic, amphoteric, zwitterionic and anionic surfactants, and c) optionally 0.1-10 parts by weight of one or more components selected from the following thickeners, fragrances, preservatives, colorants, vegetable extracts, and other additives and auxiliaries; and d) water to 100.

11. An aqueous shower and hair shampoo, comprising a) 1-10 parts by weight of a compound of the general formula (1) of claim 1;

b) 1-20 parts by weight of at least one surfactant selected from the group consisting of nonionic, amphoteric, zwitterionic and anionic surfactants; and c) 0.1-10 parts by weight of one or more components selected from the following thickeners, fragrances, preservatives, colorants, vegetable extracts and other additives and auxiliaries and optionally d) water to 100.

12. An aqueous washing-up liquid, comprising a) 1-10 parts by weight of at least one compound of the general formula (1) of claim 1;

b) 1-30 parts by weight of at least one surfactant selected from the group consisting of nonionic, amphoteric, zwitterionic and anionic surfactants; and c) optionally 0.1-10 parts by weight of one or more components selected from the following thickeners, fragrances, preservatives, colorants, vegetable extracts and other additives and auxiliaries and optionally d) water to 100.

13. A skin-care agent, comprising a) 1-10 parts by weight of at least one compound of the general formula (1) of claim 1;

b) 1-10 parts by weight of at least one surfactant selected from the group consisting of nonionic, amphoteric, zwitterionic and anionic surfactants; and c) optionally 2-10 parts by weight of one or more components selected from the group consisting of vegetable oils, mineral oils, and ester oils;

d) 1-5 parts by weight of a consistency-imparting agent;

e) 0.5-5.0 parts by weight of one or more components selected from the following fragrances, colorants, and preservatives; and f) water to 100.

14. A skin-cleaning agent, comprising a) 1-10 parts by weight of at least one compound of the general formula (1) of claim 1;

b) 0.1-20 parts by weight of at least one surfactant selected from the group consisting of nonionic, amphoteric, zwitterionic and anionic surfactants; and c) optionally 0.1-10 parts ,by weight of one or more components selected from the following thickeners, fragrances, preservatives, colorants, vegetable extracts and other additives and auxiliaries and optionally d) water to 100.

* * * * *